United States Patent [19]

Scaringe

[11] Patent Number: 6,111,086
[45] Date of Patent: Aug. 29, 2000

[54] ORTHOESTER PROTECTING GROUPS

[76] Inventor: Stephen A. Scaringe, 2835 Northbrook, Apt. B, Boulder, Colo. 80304

[21] Appl. No.: 09/032,623

[22] Filed: Feb. 27, 1998

[51] Int. Cl.$^7$ .................................................. C07H 17/00
[52] U.S. Cl. .................... 536/22.1; 536/23.1; 536/25.33; 536/25.34; 536/26.26; 536/26.7; 536/26.71; 536/26.72; 536/26.73; 536/26.74
[58] Field of Search .................. 536/22.1, 23.1, 536/25.33–25.34, 26.26, 26.7, 26.71–26.74, 27.6, 27.8, 27.81, 28.4, 28.5, 28.53, 28.54, 124, 126

[56] References Cited

U.S. PATENT DOCUMENTS

| | | | |
|---|---|---|---|
| 4,415,732 | 11/1983 | Caruthers et al. | 536/27 |
| 4,458,066 | 7/1984 | Caruthers et al. | 536/27 |

OTHER PUBLICATIONS

Rastogi, H., et al., "A new 2'–hydroxyl protecting group for the automated synthesis of oligoribonucleotides," Nucleic Acids Res., 23, pp. 4872–4877 (1995).

Capaldi, et al., "Use of the 1–(2–fluorophenyl)–4–methoxypiperidin–4–yl (Fpmp) and related protecting groups in oligoribonucleotide synthesis: stability of internucleotide linkages to aqueous acid," Nucleic Acids Res., 22, pp. 2209–2216 (1994).

Rao, M.V., et al, "Use of the 1–(2–Fluorophenyl)–4–methoxypiperidin–4–yl (Fpmp) protecting group in the solid–phase synthesis of oligo– and poly–ribonucleotides," J. Chem. Soc. Perkins Trans., 2, pp. 43–55 (1993).

Hata, T., et al, "2–chloroethyl orthoformate as a reagent for protection in nucleotides synthesis," Tetrahedron Lett., 51, pp. 4443–4446 (1969).

Sakatsume, O., et al, "Synthesis and properties of non–hammerhead RNA using 1–(2–chloroethoxy)–ethyl group for the protection of 2'–hydroxyl function," Nucleosides & Nucleotides, 10, pp. 141–153 (1991).

Sekine, M. et al, "Cyclic orthoester functions as new protecting groups in nucleosides," J. Am. Chem. Soc., 105, 2044–2049 (1983).

Beaucage, S.L., et al, "Advances in the synthesis of oligonucleotides by the phosphoramidite approach," Tetrahedron, 48, pp. 2223–2311 (1992).

*Primary Examiner*—James O. Wilson
*Assistant Examiner*—Howard Owens
*Attorney, Agent, or Firm*—Swanson & Bratschun LLC

[57] ABSTRACT

Novel orthoesters are provided which can be used as a 2'-hydroxyl protecting groups or 2'-modification in the synthesis of polymers containing ribonucleic acid (RNA) nucleotides. The RNA comprising the orthoester can be handled and analyzed while 2'-modified, thereby minimizing potential degradation. The orthoester is stable during oligonucleotide synthesis. The orthoester is subsequently modified and can then be removed under mild acidic conditions. The ease and dependability of this process and the quality of the RNA product synthesized with this invention are comparable to that previously associated only with DNA synthesis.

19 Claims, 2 Drawing Sheets

ORTHOESTER PROTECTING GROUPS

TECHNICAL FIELD

The present invention relates to the field of protecting groups in organic synthesis and, more particularly, to the use of these compounds as ribonucleoside protecting groups and as 2'-modifications. Still more specifically, the protecting groups are used in the synthesis of oligonucleotides containing ribonucleotide subunits.

BACKGROUND OF THE INVENTION

The ability to routinely synthesize ribonucleic acid (RNA) has become increasingly important as research reveals the multitude of RNA's biological functions. There are many types of RNA including ribosomal RNA, transfer RNA and messenger RNA. RNA also is important in various structures and functions as well as being a catalyst in enzymatic reactions, as in the case of ribozymes. Because of the important biological roles RNA plays, both known and unknown, it is of considerable utility to be able to synthesize short (2–300 nucleotides) defined sequences of RNA, commonly referred to as RNA oligonucleotides or oligoribonucleotides. Over the past 25 years, many chemical approaches have been explored for synthesizing RNA oligonucleotides. Because deoxyribonucleic acid (DNA) methodologies have progressed more rapidly, the usual strategy for the synthesis of RNA has been to adapt DNA chemistries to RNA synthesis. Consequently, most approaches have focused on retaining the 5'-dimethoxytrityl (DMT) ether and adding a compatible 2'-hydroxyl protecting group such as fluoride-labile silyl ethers, photo-labile moieties, and acid-labile acetals. A delicate balance has been required to successfully utilize the acid-labile 2'-acetals in conjunction with the acid-labile 5'-DMT ether. Therefore, other approaches have involved retaining the 2'-acetal while replacing the 5'-DMT.

The acid-labile acetals have many attractive features. For example, it has been reported that it is possible to chromatograph some 2'-acetal-protected RNA. However, the subsequent removal of these acetals, which are used with the DMT group, requires acidic conditions which subsequently cause degradation of the RNA, or require extremely long periods of time to remove (>24 hours). Therefore, although it may be possible to safely handle and purify some 2'-acetal-protected RNAs, the harsh conditions required for rapid deprotection may require further purification of the RNA, thereby negating this advantage. Milder conditions can be used but these are inconvenient, requiring more than 24 hours. More-labile acetals can not be used as they would not be sufficiently stable to the DMT acid-deprotection conditions during RNA synthesis.

Of all of the RNA synthesis methods reported to date, only the 5'-DMT-2'-t-butyldimethylsilyl (TBDMS) and the 5'-DMT-2'-[1-(2-fluorophenyl)-4-methoxypiperidin-4-yl] (FPMP) chemistries are readily available commercially. Unfortunately, neither of these methods allows RNA synthesis to be as routine and dependable as DNA synthesis. The impediments facing 5'-DMT-2'-FPMP chemistry are related to the problem of balancing two acid-labile protecting groups. One of the major difficulties with the 2'-TBDMS approach is that stepwise coupling yields are only 96–98% under routine conditions compared to >99% for DNA. These methods enable the synthesis of RNA in acceptable yields and quality, but a high level of skill and significant investments in training and experience are required to deliver adequate results.

One of the most desirable conditions for the final 2'-deprotection of synthesized RNA is an extremely-mildly-acidic aqueous solution. In the optimal scheme, the 2'-protecting groups only have to be stable to withstand oligonucleotide synthesis conditions. Scaringe and Caruthers (U.S. patent application Ser. No. 08/488,878, filed Jun. 9, 1995 and incorporated herein by reference) recently reported a novel RNA synthesis strategy similar to such a scheme. Their investigations led to the development of silyl ethers for protection of the 5'-hydroxyl. However, this 5'-silyl ether oligonucleotide synthesis chemistry was not compatible with mildly-acid-labile 2'-acetals. Acid-labile orthoester protecting groups were investigated and discovered to have potential for use at the 2'-hydroxyl. The 2'-orthoesters that were developed in conjunction with 5'-silyl ethers enabled the synthesis of RNA oligonucleotides. Scaringe and Caruthers disclose specific orthoester protecting groups at the 2'-position of ribonucleotides. However, they do not disclose the orthoesters of the present invention.

The present invention provides an orthoester moiety that serves as a protecting group, particularly for RNA synthesis. Also provided in this invention is RNA comprising the protecting group which possesses novel advantages and useful features, e.g., a modified RNA oligonucleotide that is easily handled and analyzed with minimal concern about degradation. The protecting groups can be readily cleaved (<10 minutes), if so desired, under extremely mild conditions that cause no detectable degradation of the RNA. No prior art anticipates that the following 2'-modification

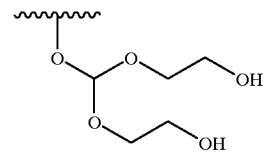

would be advantageous to RNA synthesis. This 2'-modification is the result of using an orthoester of the following general structure:

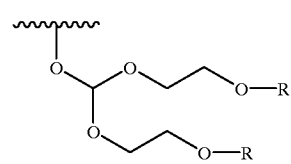

where R represents protecting groups which can be removed prior to removing the orthoester.

The prior art has provided several means to synthesize RNA oligonucleotides. However, none have enabled the synthesis, handling, analysis and use of RNA oligonucleotides to be as robust and dependable as DNA synthesis, nor produced RNA comparable to the high quality in which DNA can be produced. No prior art has disclosed a modification of RNA that enables the RNA to be easily handled and then where the modification, e.g., a protecting group, can be removed under mild conditions to yield fully deprotected RNA. The present invention, therefore, provides more robust RNA synthesis methods which consistently produce higher quality RNA on a routine basis.

SUMMARY OF THE INVENTION

Accordingly, it is an object of this invention to provide useful protecting groups for the improved synthesis, analysis, handling and use of RNA oligonucleotides or other polymers containing ribonucleotides. It is a further objective of this invention to provide RNA, comprising such protecting groups, that can be easily analyzed, handled and used without requiring extensive safeguards against degradation. The protecting groups can be subsequently removed if desired under extremely mild conditions to yield high-quality fully deprotected RNA. Those skilled in the art can use these protecting groups in other organic synthesis methodologies as well. Therefore, this invention is not limited to the field of nucleic acid and oligonucleotide chemistry.

The present invention achieves these and other objectives by the provision of novel orthoester protecting groups with innovative and useful features. We have developed, for example, the O-bis(2-acetyl-ethoxy)methyl (ACE) orthoester:

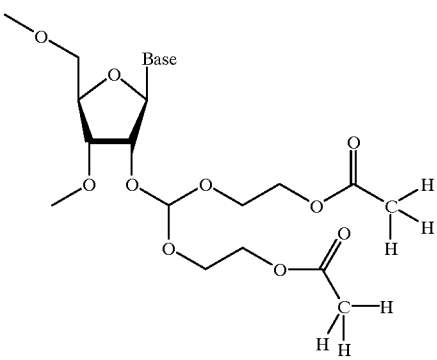

that is stable to nucleoside and oligonucleotide synthesis conditions but is modified via ester hydrolysis during base deprotection of the oligonucleotide or polymer. The resulting 2'-bis(2-hydroxyethyl)methyl orthoester protecting group (2'-EG):

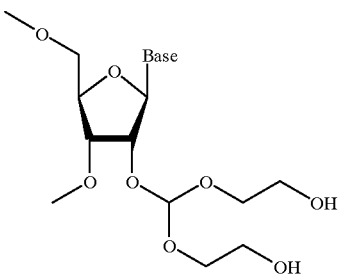

is 10 times more labile to acid than it's precursor, the ACE orthoester. Complete cleavage of the 2'-EG orthoester may be effected using extremely mild conditions (pH 3, <10 min., 55° C.). The innovative features of this chemistry have enabled the synthesis of RNA oligonucleotides surpassing results in the prior art in terms of quality.

The orthoesters of the present invention are illustrated as follows:

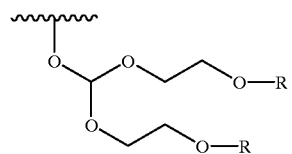

where R represents protecting groups which can be removed prior to removing the orthoester. An example of an orthoester with appropriate R groups is as follows:

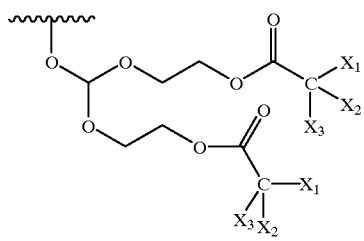

where $X_1$, $X_2$, and $X_3$ are appropriate atoms or ligands. Several suitable orthoesters are illustrated as follows:

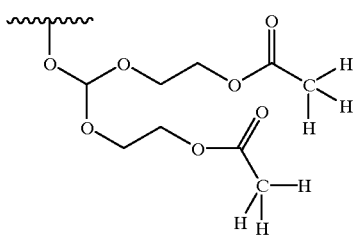

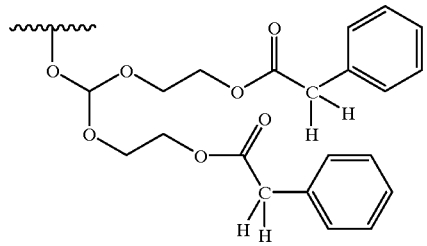

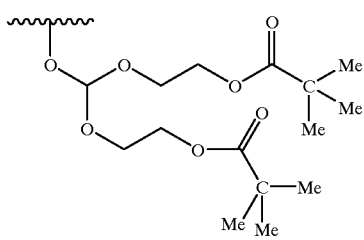

The general structure of a ribonucleoside of this invention is illustrated as follows:

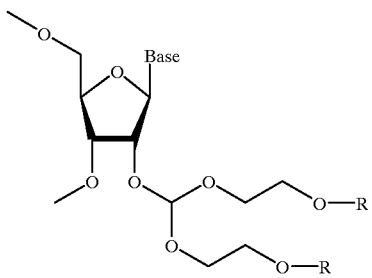

where exocyclic amines, 5'-hydroxyl and the 3'-hydroxyl groups are appropriately protected and/or functionalized for use in oligonucleotide synthesis and R represents protecting groups which can be removed while leaving the 2'-orthoester moiety intact. More specifically, the general structure of a ribonucleoside of this invention has the following structure where the R groups from above are acyl protecting groups and $X_1, X_2$, and $X_3$ are appropriate atoms or ligands:

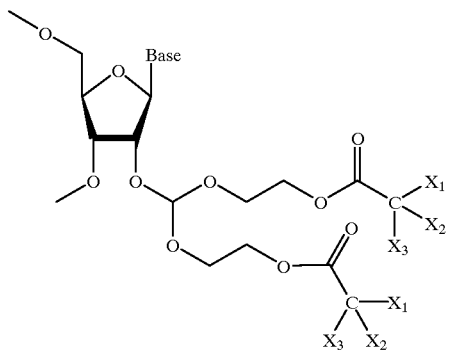

The ACE orthoester comprises protecting groups. No prior art describes the use of protected orthoesters in oligonucleotide synthesis. It was not known that an orthoester utilizing, for example, protected ethylene glycol ligands would be stable to oligonucleotide synthesis conditions. It also was not known that orthoesters would be significantly more labile once protecting groups were removed from the ethylene glycol ligands. The novel orthoesters have been utilized for the synthesis of RNA of higher quality than that disclosed in prior art. Furthermore, this invention has made it possible to synthesize, handle, analyze and use RNA with ease comparable to DNA. Some useful aspects of this invention are as follows:

(1) It is possible to analyze and handle RNA while it is still 2'-protected. The structure of a typical ribonucleotide in a polymer of the present invention has the 2'-EG modified structure:

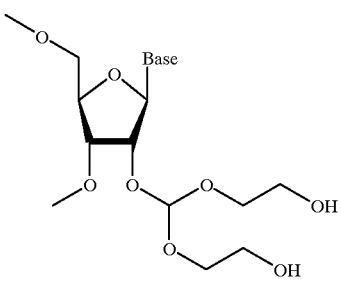

The ability to analyze and handle polymers containing the 2'-EG-modified ribonucleotide subunit is important for two major reasons: (a) The 2'-modified RNA is relatively stable to degradation. Therefore, it is not necessary to observe stringent sterile conditions while handling, analyzing and purifying 2'-modified RNA synthesized using this invention. (b) While the RNA is still 2'-modified, it is possible to analyze and purify the oligonucleotides. Over 200 sequences have been synthesized according to this invention and it has been possible to resolve every oligonucleotide into a major product during analysis. (To those skilled in the art, it is known that a percentage of RNA oligonucleotides, approximately 5–10%, can not be resolved under routine analysis conditions if the RNA is fully deprotected because of strong secondary structures and folding common to RNA.) Thus, it is possible to synthesize RNA sequences without concern over whether it will be possible to analyze the final product.

(2) The RNA quality is consistent with any sequence. For comparison, it has been reported that a 27-mer was synthesized with standard 5'-silyl-2'-orthoester chemistry in 35% overall yield. The same 27-mer was synthesized with 5'-DMT-2'-TBDMS chemistry in 45% overall yield. Using a novel orthoester of the invention, a comparable 27-mer was synthesized in >70% overall yield. A 36-mer described in a following example was routinely synthesized in 65–70% overall yield. Coupling yields of >99% were possible in <90 seconds. For many applications using RNA synthesized with this invention, it is no longer necessary to purify the RNA after synthesis as the quality of the crude RNA synthesized is sufficient for subsequent use. The high quality and high yields of RNA observed with such short coupling times are comparable with those routinely experienced in DNA synthesis.

(3) The final 2'-deprotection conditions of the RNA oligonucleotide are the mildest ever reported for this application by an order of magnitude. For example, 2'-ACE-uridine has a half life of ~7.5 minutes at pH 2, 25° C., which is comparable to previously reported orthoesters and acetals that have been used in oligonucleotide synthesis. However, when the ACE orthoester is modified by ester hydrolysis, the 2'-modified uridine is 10 times more labile with a half life of <45 seconds at pH 2, 25° C. Several assays demonstrated that there was no detectable degradation or isomerization under the extremely mild conditions used to 2'-deprotect RNA oligonucleotides synthesized according to this invention.

This invention includes several other protecting groups. For example, the following 2'-acetal protecting group is included within this invention and can be synthesized by those skilled in the art utilizing the present specification and well-known synthetic techniques.

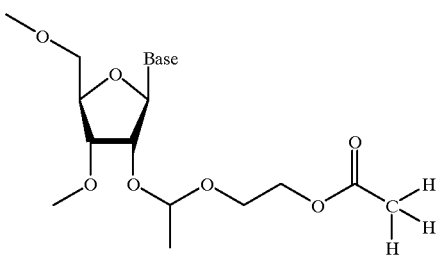

This protecting group, or variations thereof, would exhibit similar properties to the orthoester protecting groups of this invention. Therefore, this invention includes other classes of protecting groups. The present invention also provides polymers and oligonucleotides that comprise an acid-labile protecting group wherein the half life of the protecting group is as follows: the half life of that protecting group, when on the 2'-hydroxyl of a uridine nucleoside, is <3 minutes at pH 2, 25° C.

The invention also provides oligonucleotide comprising an acid-labile 2'-hydroxyl protecting group wherein the half life of the protecting group is as follows: the half life of that protecting group, when on the 2'-hydroxyl of a uridine nucleoside, is <3 minutes at pH 2, 25° C.

Further, the invention provides an oligonucleotide comprising an acid-labile 2'-hydroxyl protecting group which is itself protected by a second protecting group, and, wherein upon removal of the second protecting group(s) on the first protecting group, yield an acid-labile first protecting group wherein the half life of the first protecting group is now as follows: the half life of the deprotected first protecting group, when on the 2'-hydroxyl of a uridine nucleoside, is <3 minutes at pH 2, 25° C.

The features of the novel orthoesters of the present invention have made it possible to routinely synthesize RNA in high quality. Following synthesis, it is now possible to analyze almost any RNA oligonucleotide. Prior to this invention, this was not always possible. The RNA synthesized with this invention can be handled without the need for sterile conditions. When ready for use, the RNA is easily deprotected under extremely mild conditions that do not degrade the RNA nor contribute any detectable impurities. Oligonucleotides and polymers synthesized with this invention may be used for a wide array of purposes in various applications, including as antisense molecules, enzymatic molecules, diagnostic molecules, therapeutic molecules and research molecules. All of these uses are well known to those skilled in the art. The 2'-modification can be left on for subsequent applications, for example, analysis and purification, or it may be removed, if desired, to yield RNA with 2'-hydroxyl groups.

DETAILED DESCRIPTION OF THE INVENTION

Figure 1:
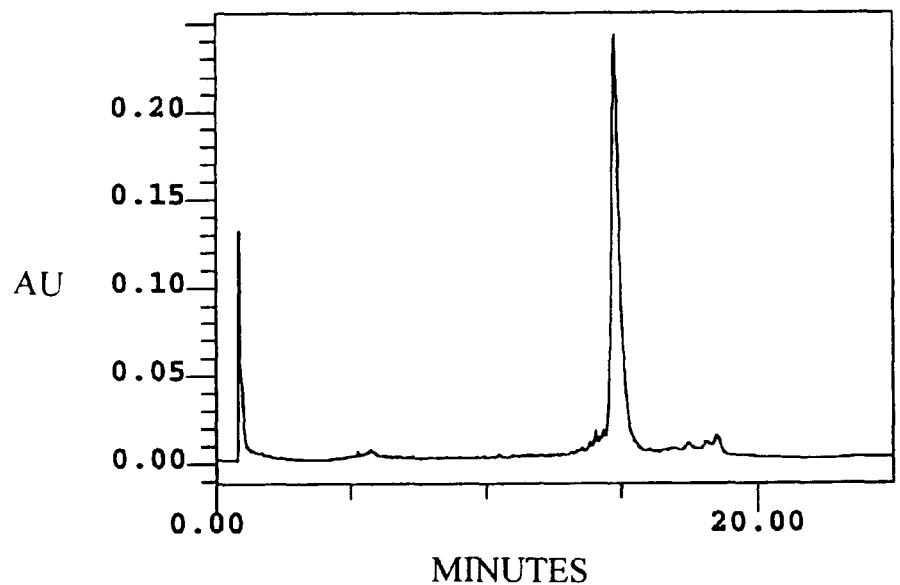
FIG. 1. Anion-exchange HPLC chromatograph of unpurified 2'-protected SEQ ID NO: 1 (2'-ACE chemistry)

As used herein, the following terms have the specified meanings:

By "atom" is meant a single element unit, either neutral or with charge, that is appropriate for the indicated position within the structure. For example, an "atom" with one bond to it may be chlorine, or hydrogen, or oxygen with a single minus charge. An "atom" with two bonds to it can be oxygen, or sulfur, or nitrogen with a minus charge.

By "ligand" is meant an organic structure comprising up to 30 atoms (not including hydrogen) of which the majority are carbon, oxygen, nitrogen.

By "orthoester" is meant a moiety or molecule comprising the following generic structure:

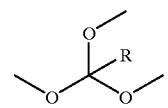

i.e., wherein three oxygen atoms are bonded to a central carbon atom and R is an atom or ligand, preferably hydrogen.

By "oligonucleotide" is meant a molecule comprising two or more nucleotides. The polynucleotide can be single, double or multiple stranded and may comprise modified or unmodified nucleotides or non-nucleotides or various mixtures and combinations thereof. Preferably the oligonucleotide comprises about 2–50 nucleotides.

By "polymer" is meant a molecule containing one or more types of subunits which may occur one, two or multiple times within the molecule, e.g. a ribonucleic acid, a peptide-nucleic acid hybrid.

By "phosphorus moiety" is meant a group of atoms comprising one or more phosphorus atoms. Preferably, the total number of all atoms in this group is less than 40 (not including hydrogen).

By "protecting group" is meant a group of atoms which purpose is to temporarily mask the functionality of the site to which it is attached on a molecule. Prior to the use of the molecule in a subsequent analysis or application, the protecting group may or may not be removed.

By "functional group" is meant a site on a molecule that has, as known to those skilled in the art, the potential to participate in reactions. Functional groups include, for example, hydroxyls, amines, thiols, halogens, phosphoramidites.

By "nucleotide" is meant, as recognized in the art, natural bases (standard), and modified bases well known in the art. Such bases are generally located at the 1' position of a sugar moiety. A nucleotide generally comprises a base, sugar and a phosphate group. The nucleotides can be unmodified or modified at the sugar, phosphate and/or base moiety (also referred to interchangeably as nucleotide analogs, modified nucleotides, non-natural nucleotides, non-standard nucleotides and other).

The symbol as used in structural drawings represents that the line that is immediately perpendicular to this symbol is a bond to another atom or atom within a larger molecule.

By "phosphoramidite" is meant the functional moiety as first disclosed by Caruthers and Beaucage (U.S. Pat. No. 4,415,732).

By "enzymatic nucleic acid molecule" is meant a molecule, comprising at least one nucleic acid, capable of catalyzing (altering the velocity and/or rate of) one or more reactions, for example, the cleavage of separate nucleic acid molecules in a nucleotide specific manner. The term enzymatic nucleic acid molecule can be used interchangeably, for example, with phrases such as ribozymes, catalytic RNA, enzymatic RNA, catalytic DNA, catalytic oligonucleotides, nucleozyme, DNAzyme, RNA enzyme, endoribonuclease, endonuclease, minizyme, leadzyme, oligozyme, or DNA enzyme.

By "modified nucleoside" or "modified nucleotide" is meant any nucleoside or nucleotide subunit which contains a modification in the chemical structure of the unmodified base, sugar and/or phosphate.

The general process for utilizing this invention is as follows. Nucleosides are suitably protected and functionalized for use in solid-phase or solution-phase synthesis of RNA oligonucleotides. The 2'-hydroxyl group in a ribonucleotide is modified using a tris orthoester reagent of this invention. (The 2'-hydroxyl is modified to yield a 2'-O-orthoester nucleoside of this invention by reacting the ribonucleoside with the tris orthoester reagent in the presence of an acidic catalyst, e.g., pyridinium p-toluene sulfonate. This reaction is known to those skilled in the art.) The product is then subjected to further protecting group reactions (e.g., 5'-O-silylation) and functionalizations (e.g., 3'-O-phosphitylation) to produce a desired reagent (e.g., nucleoside phosphoramidite) for incorporation within an oligonucleotide or polymer by reactions known to those skilled in the art.

A preferred embodiment of this invention is an orthoester comprising ethylene glycol ligands which are protected with acyl or ester protecting groups. More specifically, the preferred acyl group is acetyl. The nucleoside reagents may then be used by those skilled in the art to synthesize RNA oligonucleotides on commercially available synthesizer instruments, e.g. Gene Assembler Plus (Pharmacia), 380B (Applied Biosystems). Following synthesis (either solution-phase or solid-phase) of an oligonucleotide or polymer using a compound of this invention, the product is subjected to one or more reactions using non-acidic reagents. One of these reactions may be strong basic conditions, for example, 40% methylamine in water for 10 minutes at 55° C., which will remove the acyl protecting groups from the ethylene glycol ligands but leave the orthoester moiety attached. The resultant orthoester may be left attached when the polymer or oligonucleotide is used in subsequent applications, or it may be removed in a final mildly-acidic reaction, for example, 10 minutes at 55° C. in 50 mM acetic acid, pH 3.0, followed by addition of equal volume of 150 mM TRIS buffer for 10 minutes at 55° C.

The following examples are meant to be exemplary only and not limiting in any way.

EXAMPLE I

Synthesis of orthoester reagent and 5'-silyl-2'-ACE-3'-O-(N,N-diisopropylamine)-methoxyphosphine-uridine.

The reagents in this example can be obtained from a variety of commercial sources, e.g., Aldrich Chemical (Milwaukee, Wis.), TCI America (Portland, Oreg.) and Monomer Sciences (New Market, Ala.).

Synthesis of tris(2-acetyl-ethoxy) orthoformate, ACE orthoester reagent: Acetic acid ethyl ester (85%) (5 eq., 323 g) was treated with pyridinium p-toluene sulfonate (0.2 eq, 30.8 g) and trimethyl orthoformate (1 eq., 67.8 ml). The reaction was heated to distill off the methanol product. The reaction was cooled and then neutralized with base. The product was purified by column chromatography and high vacuum distillation. Final yield of product was 20%.

Synthesis of 2'-O-bis(2-acetyl-ethoxy)methyl uridine (representative of general 2'-protection reaction): 5'-O-3'-O-tetraisopropyldisiloxyl uridine (TIPS-uridine) (1 eq., 4.86 g) was reacted neat with tris(2-acetyl-ethoxy) orthoformate (2.8 eq., 9 g) and pyridinium p-toluene sulfonate (0.2 eq., 0.5 g) at 55° C. for 3 hours under high vacuum (<15 microns of Hg). The reaction was cooled to room temperature and neutralized with base. The crude reaction was passed over silica gel to do a crude purification to remove the neutralized catalyst. The enriched mixture was treated with a premixed solution of N,N,N',N'-tetramethylethylendiamine (TEMED) (9.05 ml) and 48% hydrofluoric acid (1.08 ml) in acetonitrile (100 ml) for 6 hours. The product, 2'-O-bis(2-acetyl-ethoxy) methyl uridine, was purified by column chromatography. The yield for the combined two reactions was 65%. Adenosine (N-benzoyl), cytidine (N-acetyl) and guanosine (N-isobutyrl) 2'-ACE nucleosides were similarly synthesized and similarly carried through the next two reactions to produce final nucleoside phosphoramidites for use in RNA synthesis.

Synthesis of 5'-O-silyl-2'-O-ACE-uridine: To 2'-O-ACE-uridine (1 eq., 4.9 g) and imidazole (4 eq., 2.8 g) in tetrahydrofuran was added bis(trimethylsiloxy)-cyclooctoxy-silylchloride (OCT-Cl) (1.5 eq., 5.86 g in 20 ml tetrahydrofuran) over 30 minutes with stirring. OCT-Cl can be synthesized by those skilled in the art from bis (trimethylsiloxy)-dichlorosilane and cyclooctanol. The 5'-silyl-2'-ACE uridine product was purified by silica gel chromatography and isolated in 75–85% yield.

Synthesis of 5 '-O-silyl-2'-ACE-uridine-3'-O-(N,N-diisopropylmethoxy)phosphoramidite: To a solution of 5'-O-silyl-2'-O-ACE-uridine (1 eq., 6 g) in 20 ml of dichloromethane was added first bis(N,N-diisopropylamine) methoxy-phosphine (1.3 eq., 2.7 g) followed by tetrazole (0.8 eq., 0.45 g) with stirring. After 2 hours the reaction was quenched and the product isolated in 80–90% yield via silica gel chromatography.

EXAMPLE II

Synthesis of Oligonucleotide 36 Bases in Length (SEQ ID NO: 1).

Oligonucleotide synthesis conditions were adapted from Scaringe and Caruthers, supra. Syntheses were performed on derivatized polymer supports using either a Gene Assembler Plus synthesizer (Pharmacia) or a 380B synthesizer (ABI). The protocols can be adapted by those skilled in the art to any commercially available synthesizer. The following changes were made to the protocols of Scaringe and Caruthers. The silyl deprotection reagent was replaced by 1.0 M aqueous HF, 1.6 M triethylamine (TEA) in dimethylformamide (DMF). The reaction time was 30–35 seconds. Oxidation was effected during every cycle using 3 M t-butylhydroperoxide (tBuOOH) in toluene. The wash solvents, DMF and acetonitrile (MeCN), were used between the reactions. The synthesis cycle is as follows:

| Reaction | Reagent | Time (Seconds) |
|---|---|---|
| 5'-silyl deprotection | 1.0 M HF & 1.6 M TEA in DMF | 30–35 |
| Wash | DMF | 10 |
| Wash | MeCN | 40 |

-continued

| Reaction | Reagent | Time (Seconds) |
|---|---|---|
| Couple | 15 eq. amidite/100 eq. S-ethyl-tetrazole | 90 |
| Wash | MeCN | 30 |
| Oxidize | tBuOOH | 40 |
| Wash | MeCN | 30 |
| Capping | 10% acetic anhydride & 10% N-Methyl imidazole | 30 |
| Wash | MeCN | 30 |
| Wash | DMF | 5 |

Figure 2:
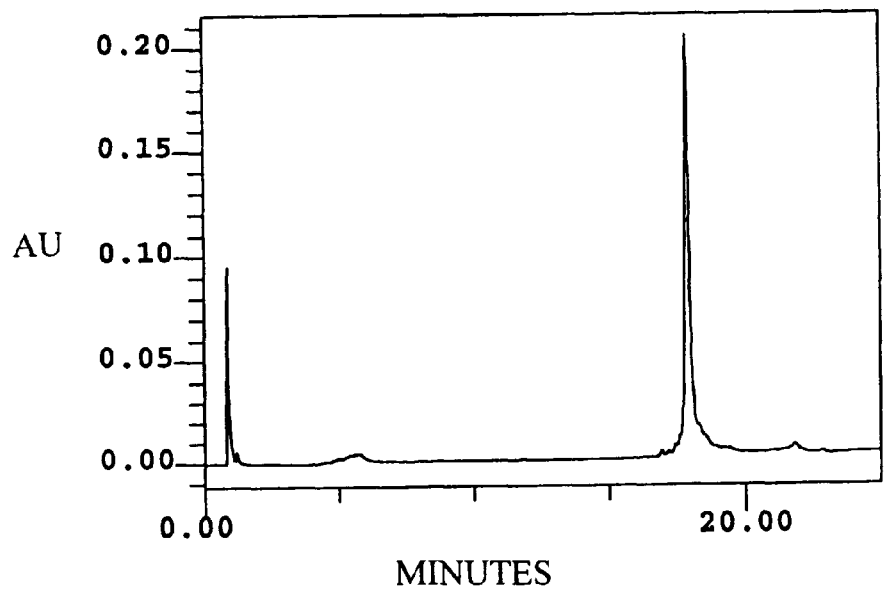
FIG. 2. Anion-exchange HPLC chromatograph of fully deprotected SEQ ID NO: 1 (2'-ACE chemistry)
Figure 3:
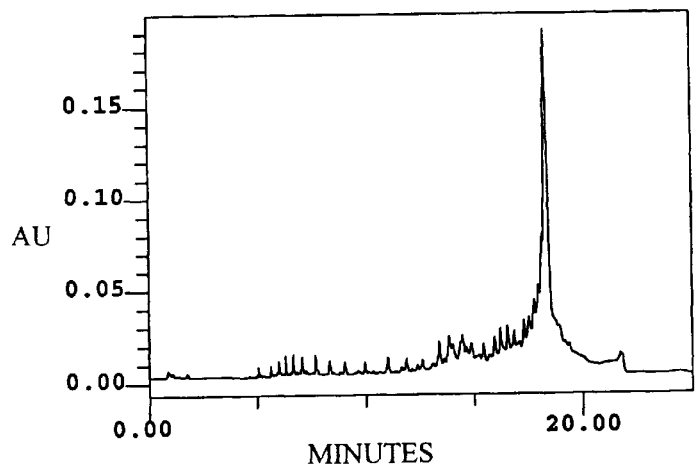
FIG. 3. Anion-exchange HPLC chromatograph of fully deprotected SEQ ID NO: 1 (5'-DMT-2'-TBDMS chemistry)

Following synthesis on the synthesizer, the polymer support is treated for 30 minutes using a 1 M solution of disodium-2-cobamoyl-2-cyanoethylene-1,1-dithiolate trihydrate ($S_2Na_2$) in DMF. For a 0.2 micromole synthesis of SEQ ID NO: 1, 1 ml of this reagent was used to cleave the methyl protecting groups from the phosphates. The $S_2Na_2$ reagent was washed out with water and acetone. The dried support was treated with 1 ml of 40% N-methylamine in water for 10 minutes at 55° C. to cleave all base-labile protecting groups and release the 2'-protected SEQ ID NO: 1 RNA oligonucleotide into solution. The crude reaction mixture was analyzed by anion exchange high pressure liquid chromatography (HPLC) and the result illustrated in FIG. 1. From these results it can be seen that the 2'-protected oligonucleotide can be clearly analyzed by HPLC. The crude SEQ ID NO: 1 reaction in methylamine and water was dried down in vacuo. The pellet was resuspended in 1.6 ml of 50 mM acetic acid, pH 3.0, and incubated for 10 minutes at 55° C. To this was added 1.6 ml of 150 mM TRIS, pH 8.7, (Final pH of solution 7.7–8.0) for 10 minutes at 55° C. An aliquot of this solution was then analyzed by identical HPLC conditions and the result illustrated in FIG. 2. The same SEQ ID NO: 1 was synthesized and provided from a commercial source which synthesized the oligonucleotide using commercially available 5'-DMT-2'-TBDMS chemistry. The crude product was analyzed under identical HPLC conditions and the result illustrated in FIG. 3. Direct analytical comparison of the crude SEQ ID NO: 1 produced using this invention (FIG. 2) and the current state-of-the-art 5'-DMT-2'-TBDMS chemistry (FIG. 3) demonstrates the improved quality now possible with this invention.

EXAMPLE III

Synthesis and HPLC analysis of SEQ ID NO: 2

Figure 4:
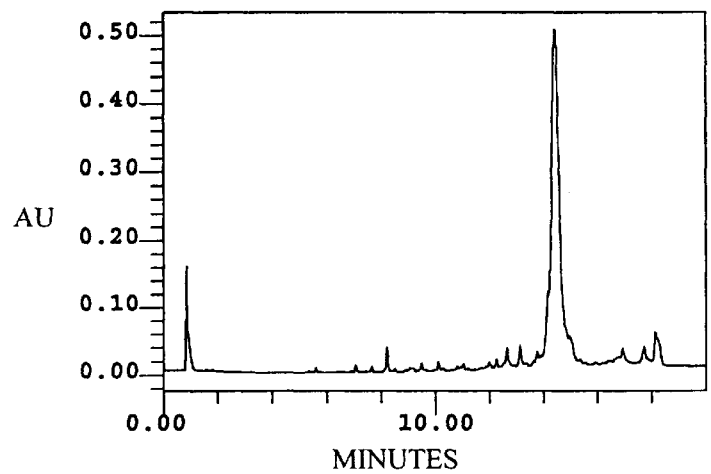
FIG. 4. Anion-exchange HPLC chromatograph of unpurified 2'-protected SEQ ID NO: 2
Figure 5:
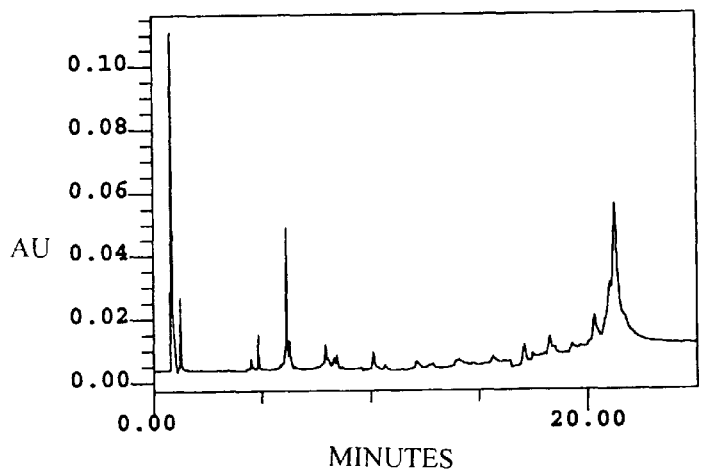
FIG. 5. Anion-exchange HPLC chromatograph of fully deprotected SEQ ID NO: 2

SEQ ID NO: 2 was synthesized using the methodology in Example II above. The 2'-orthoester crude RNA was analyzed by HPLC (FIG. 4). The HPLC result illustrates a clear major product in 85% yield. The 2'-orthoester crude RNA was treated as in example II to remove the 2'-orthoester modification. The product was then analyzed under identical HPLC conditions (FIG. 5) but no major product was observed. The product was also analyzed under highly denaturing conditions using polyacrylamide gel electrophoresis (PAGE) with 7 M urea at 60° C. In this analysis a major distinct product band was observed as would be expected for a 14-nucleotide RNA oligonucleotide (results not shown).

All other commercially available means of synthesizing RNA produce RNA that can only be easily analyzed when fully deprotected. When the final RNA product can not be easily analyzed, then these results illustrate the need for this invention to provide a dependable and conclusive means to analyze RNA oligonucleotides. As this example demonstrates it is of significant utility to use this invention to be able to handle and analyze RNA while still 2'-modified.

What is claimed is:

1. An oligonucleotide comprising a moiety of the formula:

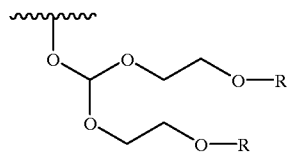

wherein R is any appropriate ligand that protects the oxygen.

2. An oligonucleotide comprising the structure:

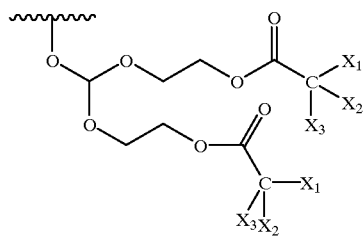

wherein $X_1$, $X_2$, $X_3$ are the same or different and are any atoms, selected from the group consisting of Cl, H, O, S and N or appropriate ligands.

3. An oligonucleotide according to claim 2 wherein $X_1$, $X_2$, $X_3$ are hydrogen.

4. An oligonucleotide according to claim 1 wherein R is hydrogen.

5. An oligonucleotide wherein a functional group has attached thereto the structure:

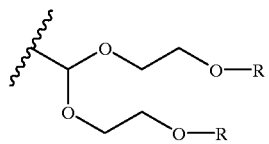

wherein R is hydrogen or any appropriate ligand that protects the oxygen.

6. An oligonucleotide comprising the following structure:

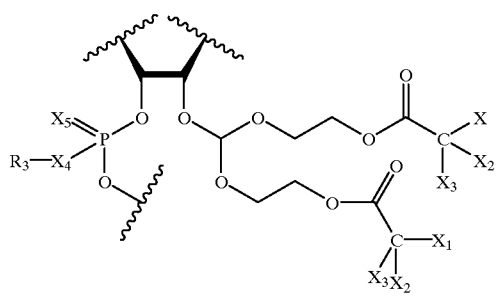

wherein $R_3$ is any appropriate ligand, $X_4$ and $X_5$ are the same or different atom, selected from the group consisting of Cl, H, O, S and N and wherein $X_1$, $X_2$, $X_3$ are the same or different and are any atoms, selected from the group consisting of Cl, H, O, S and N or appropriate ligands.

7. An oligonucleotide according to claim 6 wherein $X_4$ and $X_5$ are oxygen.

8. An oligonucleotide according to claim 6 wherein $R_3$ is nothing.

9. An oligonucleotide according to claim 6 wherein $X_4$ and $X_5$ are oxygen.

10. An oligonucleotide according to claim 6 wherein $X_4$ and $X_5$ are oxygen and wherein $X_1$, $X_2$, and $X_3$ are hydrogen.

11. An oligonucleotide according to claim 10 wherein $R_3$ is nothing.

12. An oligonucleotide comprising the following structure,

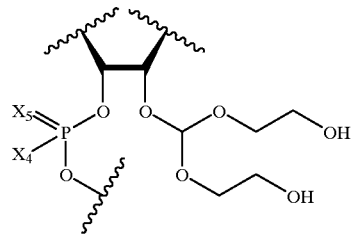

wherein $X_4$ and $X_5$ are the same or different atom, selected from the group consisting of Cl, H, O, S and N.

13. An oligonucleotide according to claim 12 wherein $X_4$ and $X_5$ are oxygen.

14. A process to synthesize polymers or oligonucleotides which utilizes any of the compounds, polymers or oligonucleotides according to any of the preceding claims.

15. A process to synthesize polymers or oligonucleotides which utilizes any of the compounds, structures and modifications as in any of the preceding claims and wherein the internucleotide linkage(s) is(are) oxidized before completion of oligonucleotide synthesis.

16. A process according to claim 15 wherein the internucleotide linkage is oxidized every cycle or the majority of cycles.

17. A compound of the formula:

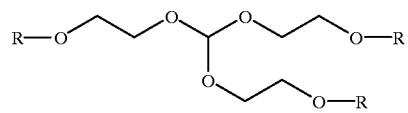

wherein R is selected from the group consisting of an ester, carbonate, silyl ether and sulfonate.

18. A compound according to claim 17 wherein R is

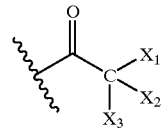

wherein $X_1$, $X_2$, $X_3$ are the same or different and are any atoms or ligands.

19. A compound according to claim 18 wherein $X_1$, $X_2$, $X_3$ are hydrogen.

* * * * *

SEQUENCE LISTING

```
<160> NUMBER OF SEQ ID NOS: 2

<210> SEQ ID NO 1
<211> LENGTH: 36
<212> TYPE: RNA
<213> ORGANISM: Artificial Sequence
<220> FEATURE:
<223> OTHER INFORMATION: Description of Artificial Sequence: Other nucleic
      acid

<400> SEQUENCE: 1
ucuccaucug augaggccga aaggccgaaa aucccc                                    36

<210> SEQ ID NO 2
<211> LENGTH: 14
<212> TYPE: RNA
<213> ORGANISM: Artificial Sequence
<220> FEATURE:
<223> OTHER INFORMATION: Description of Artificial Sequence: Other nucleic
      acid

<400> SEQUENCE: 2
gggaacgucu aggg                                                            14
```